(12) United States Patent
Eidenschink (10) Patent No.: US 7,378,048 B2
(45) Date of Patent: May 27, 2008

(54) METHOD FOR FORMING CATHETER CURVES

(75) Inventor: Thomas C. Eidenschink, Rogers, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 906 days.

(21) Appl. No.: 10/308,720

(22) Filed: Dec. 3, 2002

(65) Prior Publication Data

US 2004/0104512 A1    Jun. 3, 2004

(51) Int. Cl.
*B29C 67/00* (2006.01)

(52) U.S. Cl. .............. 264/486; 264/403; 264/485; 264/285; 264/295; 264/339

(58) Field of Classification Search ........... 264/405, 264/479, 480, 241, 259, 263, 267, 285; 156/272.2, 156/293, 294
See application file for complete search history.

(56) References Cited

U.S. PATENT DOCUMENTS

| | | | |
|---|---|---|---|
| 2,393,541 A | * | 1/1946 | Kohler ............... 219/634 |
| 3,993,529 A | * | 11/1976 | Farkas ............... 156/380.7 |
| 4,093,484 A | * | 6/1978 | Harrison et al. ....... 156/244.13 |
| 4,292,270 A | | 9/1981 | Hannah et al. |
| 4,359,453 A | | 11/1982 | Gordon |
| 4,590,922 A | | 5/1986 | Gordon |
| 4,622,953 A | | 11/1986 | Gordon |
| 4,627,436 A | | 12/1986 | Leckrone |
| 4,643,186 A | | 2/1987 | Rosen et al. |
| 4,654,024 A | | 3/1987 | Crittenden et al. |
| 4,672,962 A | | 6/1987 | Hershenson |
| 4,685,458 A | | 8/1987 | Leckrone |
| 4,735,796 A | | 4/1988 | Gordon |
| 4,747,405 A | | 5/1988 | Leckrone |
| 4,748,979 A | | 6/1988 | Hershenson |
| 4,767,611 A | | 8/1988 | Gordon |
| 4,790,311 A | | 12/1988 | Ruiz |

(Continued)

FOREIGN PATENT DOCUMENTS

EP    0 417 865 A1    3/1991

(Continued)

OTHER PUBLICATIONS

Suwanwatana, W., Research Poster—University of Delaware "Inductions Heating of Thin Films Containing Ferromagnetic Particles", www.ccm.udel.edu/publications/AR/posters/PS/Suwanwatana, Mar. 18, 2002, 2 pages.
Gleich, Bernhard, "Catheter Temperature Mesurement with Ferromagnets," *Research Disclosure*, Feb. 2001, p. 189.

*Primary Examiner*—Christina Johnson
*Assistant Examiner*—Jeff Wollschlager
(74) *Attorney, Agent, or Firm*—Crompton, Seager & Tufte, LLC (57) ABSTRACT

A method and apparatus for forming catheters and catheter curves using ferromagnetic materials exposed to an alternating magnetic field. Heat is generated in the exposed ferromagnetic material. The temperature of the ferromagnetic material is allowed to reach a desired temperature, preferably the Curie temperature of the ferromagnetic material containing portion. The heat generated is transferred to a catheter, wherein the catheter can be selectively formed or assembled and bonded at the desired elevated temperature.

10 Claims, 8 Drawing Sheets

U.S. PATENT DOCUMENTS

| | | | |
|---|---|---|---|
| 4,807,620 A | 2/1989 | Strul et al. | |
| 4,923,437 A | 5/1990 | Gordon | |
| 4,954,678 A * | 9/1990 | Harmony et al. | 219/769 |
| 5,041,089 A | 8/1991 | Mueller et al. | |
| 5,047,025 A | 9/1991 | Taylor et al. | |
| 5,087,256 A | 2/1992 | Taylor et al. | |
| 5,098,429 A | 3/1992 | Sterzer | |
| 5,190,540 A | 3/1993 | Lee | |
| 5,368,591 A | 11/1994 | Lennox et al. | |
| 5,391,595 A * | 2/1995 | Clark et al. | 523/300 |
| 5,422,048 A * | 6/1995 | Kodama et al. | 264/443 |
| 5,504,308 A * | 4/1996 | Shiozaki | 219/634 |
| 5,578,008 A | 11/1996 | Hara | |
| 5,626,136 A | 5/1997 | Webster, Jr. | |
| 5,830,224 A | 11/1998 | Cohn et al. | |
| 5,891,094 A | 4/1999 | Masterson et al. | |
| 5,971,979 A | 10/1999 | Joye et al. | |
| 5,988,689 A * | 11/1999 | Lever | 285/21.1 |
| 6,006,756 A | 12/1999 | Shadduck | |
| 6,027,450 A | 2/2000 | Brown et al. | |
| 6,056,844 A * | 5/2000 | Guiles et al. | 156/272.4 |
| 6,123,718 A | 9/2000 | Tu et al. | |
| 6,179,824 B1 | 1/2001 | Eggers et al. | |
| 6,210,393 B1 | 4/2001 | Brisken | |
| 6,272,371 B1 * | 8/2001 | Shlomo | 600/424 |
| 6,287,320 B1 | 9/2001 | Slepian | |
| 6,319,244 B2 * | 11/2001 | Suresh et al. | 604/525 |
| 6,355,029 B1 | 3/2002 | Joye et al. | |
| 6,387,052 B1 | 5/2002 | Quinn et al. | |
| 6,428,534 B1 | 8/2002 | Joye et al. | |
| 6,428,563 B1 | 8/2002 | Keller | |
| 6,464,684 B1 * | 10/2002 | Galdonik | 604/527 |
| 6,468,297 B1 | 10/2002 | Williams et al. | |
| 6,585,924 B1 * | 7/2003 | Harget et al. | 264/230 |
| 6,776,949 B2 * | 8/2004 | Weber | 264/402 |
| 2002/0026192 A1 | 2/2002 | Joye et al. | |
| 2002/0165520 A1 | 11/2002 | Forman | |
| 2003/0226631 A1 * | 12/2003 | Sterud et al. | 156/64 |
| 2004/0021249 A1 * | 2/2004 | Weber et al. | 264/248 |

FOREIGN PATENT DOCUMENTS

| | | | |
|---|---|---|---|
| JP | 405185472 | * | 7/1993 |
| JP | 10156942 | * | 6/1998 |
| JP | 410156942 A | * | 6/1998 |
| WO | WO99/03306 | * | 1/1999 |

* cited by examiner

METHOD FOR FORMING CATHETER CURVES

FIELD OF THE INVENTION

The present invention is related generally to medical devices. More specifically, the present invention is related to catheters. The present invention includes apparatus and methods for forming catheters and catheter curves.

BACKGROUND OF THE INVENTION

A wide variety of intravascular catheters have been developed to diagnose and treat vascular diseases. Some types of catheters include a curved or shaped distal portion. The curved or shaped portion is used in order to facilitate navigation of the catheter through the vasculature. The curved or shaped portion allows the catheter to make sharp bends or follow tortuous passages not easily achieved using other catheters.

Some catheters used for diagnosing and treating vascular diseases are generally comprised of an inner layer, a reinforcing layer, and an outer layer. The outer layer may include a plurality of segments placed along the length of the catheter. The segments may have different mechanical properties and/or materials, thus varying the rigidity, flexibility, and torqueability of the catheter along its shaft. For example, in selecting a useful combination of segments in forming the outer layer, a catheter may be created having a flexible distal region while maintaining a more rigid proximal region with a higher torqueability. The flexible distal tip region will allow the catheter to navigate tortuous regions of the vasculature while the more rigid proximal region will allow the catheter to be longitudinally pushed through the vasculature. It is necessary to bond these segments of varying properties or materials together or to the rest of the catheter shaft in order to create a generally continuous catheter shaft.

SUMMARY OF THE INVENTION

The present invention relates generally to methods for forming catheters and catheter curves and apparatus used to form catheters and catheter curves. More specifically the present invention relates to forming catheters and catheter curves using electromagnetic induction heating created by an alternating magnetic field in combination with a ferromagnetic material. The ferromagnetic material is placed in the alternating magnetic field generating heat due to hysteresis loss. The heat generated from the ferromagnetic material is transferred to a catheter tube through conduction and/or convection. Heating of catheters in contact with or in close proximity to the ferromagnetic material can be performed quickly, uniformly, and controllably.

One embodiment of the present invention includes a catheter tube and a mandrel having a ferromagnetic material. The ferromagnetic material may be embedded in the outer surface of the mandrel or contained in a coating on the mandrel. Alternatively, the mandrel may be made of a mixture of a polymer and a ferromagnetic material or the mandrel may comprise a non-ferromagnetic material having a ferromagnetic core. The mandrel may have multiple portions having different compositions or particle size or concentration of particles of a ferromagnetic material corresponding generally to segments of different materials or mechanical properties in the catheter. The mandrel may have a desired curve shape formed at the distal portion. Alternatively, the mandrel may be substantially straight or readily bendable into a desired curve shape.

The mandrel may be inserted into the lumen of the catheter tube forming a desired curve in the catheter tube, preferably at the distal end, or retaining the catheter tube substantially straight. The mandrel and the catheter tube are then exposed to an alternating magnetic field. Heat is generated in the mandrel due to the hysteresis effect from the ferromagnetic particles. The mandrel, and therefore the adjacent portion of the catheter tube, is allowed to reach a desired temperature, preferably the Curie temperature of the ferromagnetic material. The Curie temperature is the temperature above which the material becomes paramagnetic and no longer heats. A desired Curie temperature can be reached by controlling characteristics such as the particle size and the volume fraction of the ferromagnetic material. If a mandrel with multiple portions designed to reach different Curie temperatures is used, different segments of the catheter tube may reach different temperatures corresponding to desired forming or fusing temperatures related to varying melting points of the segments of the catheter tube.

Once the mandrel and the catheter tube have reached the desired temperature, they are removed from the alternating magnetic field and allowed to cool. The mandrel may then be removed from the catheter tube. A new catheter tube may be disposed on the mandrel and the forming process repeated.

Another embodiment of the invention includes a catheter tube and a fixture for containing the catheter tube. The fixture may have a top portion and a bottom portion in order to completely surround at least a portion of the catheter tube. The fixture may include a chamber designed to receive at least a portion of the catheter tube. The chamber may have a desired curve shape or may be substantially straight. The fixture may be designed to receive inserts having a chamber forming a desired curve shape. The inserts may be substituted to form additional curve shapes. The chamber or inserts may be made of or coated with a ferromagnetic material, wherein different portions of the chamber or different inserts having different compositions of the ferromagnetic material may be designed to reach different desired temperatures. The regions of varying temperatures correspond generally to different segments of the catheter comprising materials with different melting points or other mechanical properties. Certain segments can include insulating inserts placed between ferromagnetic inserts. These segments would aid in preventing overheating of a shaft segment adjacent a higher temperature insert.

At least a portion of the catheter tube may be received in the chamber of the fixture. The catheter tube, therefore, forms to the shape of the chamber. A top portion of the fixture may be placed over the catheter tube, thus enclosing at least a portion of the catheter tube. The fixture and the catheter tube are then exposed to an alternating magnetic field. Heat is generated in the fixture due to the hysteresis effect from the ferromagnetic material. The fixture, and therefore the adjacent portion of the catheter tube, is allowed to reach a desired temperature, preferably the Curie temperature of the ferromagnetic containing material. As stated above, the fixture can be precisely designed to reach a desired Curie temperature. If a fixture with multiple portions designed to reach different Curie temperatures is used, different segments of the catheter tube may reach different temperatures corresponding to varying melting or fusing temperatures or points of the segments of the catheter tube.

Once the fixture and the catheter tube have reached the desired temperature, they are removed from the alternating magnetic field and allowed to cool. The catheter tube may then be removed from the fixture. A new catheter tube may be disposed in the fixture and the forming process repeated.

Additional applications such as forming angioplasty balloons or other medical device balloons may also utilize this forming process. It may be desirable to subject different sections of a balloon to varying temperatures. For example, it may be desirable to expose the end sections to a higher temperature than the center section. A fixture using different compositions of ferromagnetic materials may be designed to allow the end sections to reach a higher Curie temperature than the center section. Exposing the fixture enclosing a balloon to an alternating magnetic field may heat the balloon portions to the desired temperatures. Following the forming of a balloon or other member, the ferromagnetic heat source may be cooled at a controlled rate to improve resulting polymer properties, as by annealing. This application may also be useful in securing the balloon end portions to a catheter shaft while not deforming the center section of the balloon.

DETAILED DESCRIPTION OF THE INVENTION

The following description should be read with reference to the drawings wherein like reference numerals indicate like elements throughout the several views. The drawings, which are not necessarily drawn to scale, depict selected embodiments and are not intended to limit the scope of the invention. Those skilled in the art will recognize that the examples may have suitable alternative embodiments that may be utilized.

Figure 1:
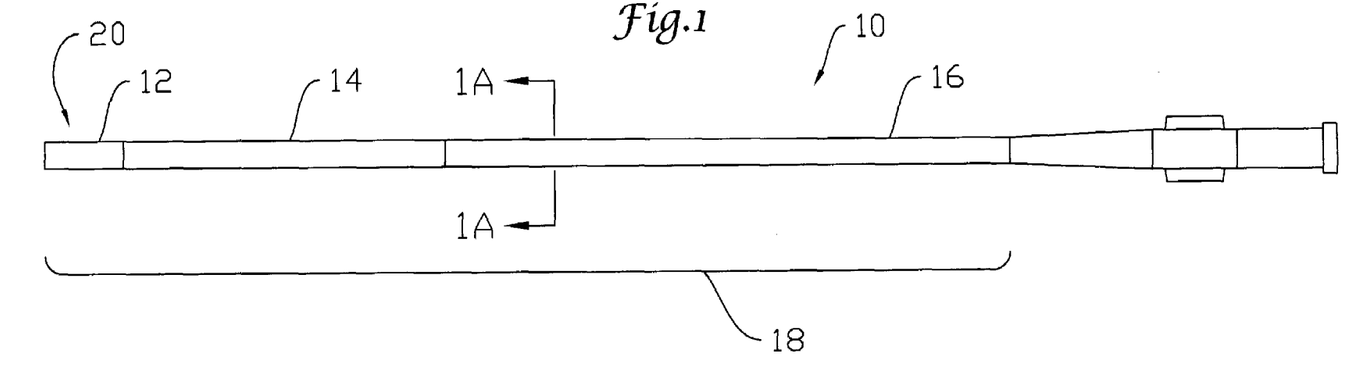
FIG. 1 is a plan view of a catheter having a plurality of segments.

FIG. 1 shows a catheter 10 having a plurality of segments 12, 14, 16. Although the catheter 10 depicted includes three segments 12, 14, 16, the invention is not limited by the number of segments of the catheter 10 or their position along the shaft 18. In one embodiment, the segments 12, 14, 16 each comprise different materials having distinct properties. However the segments may be comprised of substantially the same polymeric material having different mechanical properties. In one embodiment, the first segment 12, at the distal portion 20, is relatively flexible for navigating tortuous vasculature; the second segment 14 is somewhat less flexible; and the third segment 16 is relatively rigid to facilitate advancing the catheter through a lumen in a vasculature. The properties of the catheter 10 are only illustrative and not intended to limit the scope of the invention.

Figure 1A:
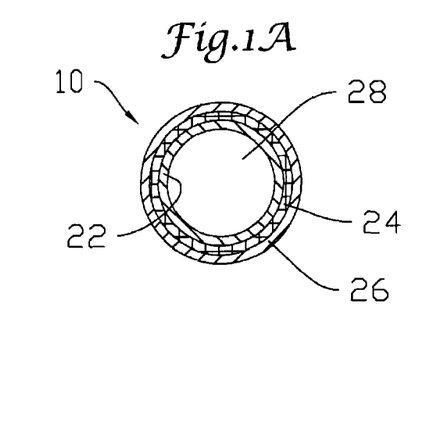
FIG. 1A is a cross-sectional view of the catheter of FIG. 1 taken along line 1A depicting multiple layers and a reinforcing member.

FIG. 1A shows a cross-sectional view of catheter 10 depicted in FIG. 1. Catheter 10 comprises an inner layer 22 having at least one lumen 28 therethrough, a reinforcing layer 24, and an outer layer 26 disposed over the reinforcing layer 24. Although catheter 10 comprises three layers 22, 24, 26, this example is only illustrative, and the invention is not limited by the number of layers or the arrangement of the layers comprising the catheter 10. In one embodiment, only the outer layer 26 includes segments 12, 14, 16 having distinctive properties.

Figure 2:
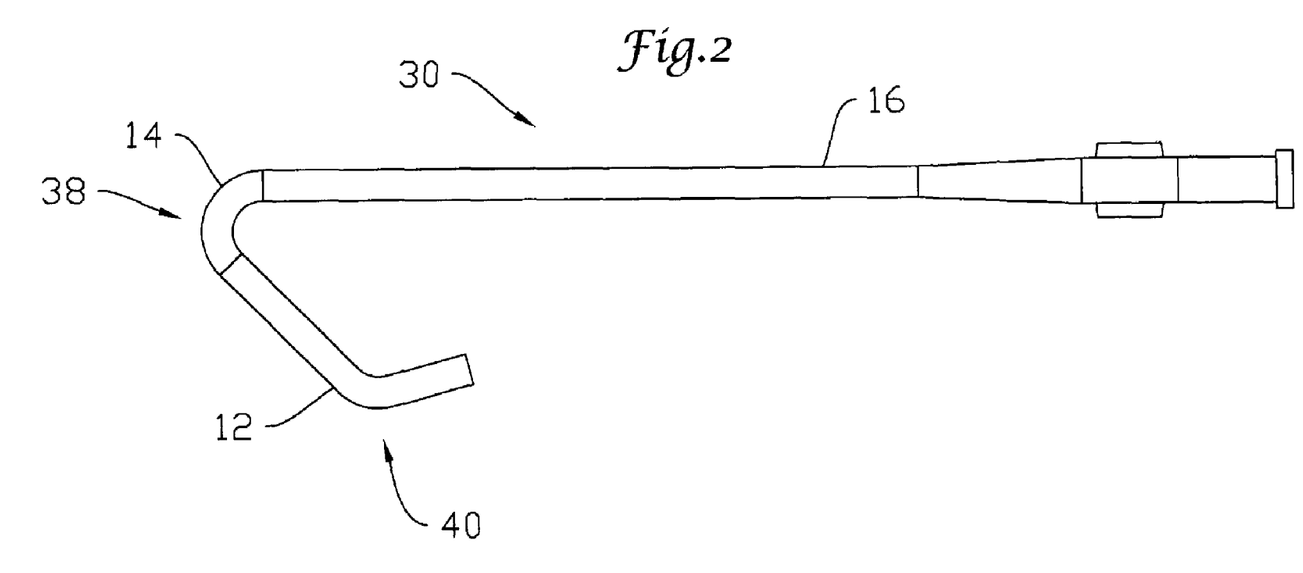
FIG. 2 is a side view of a catheter having a curved shape distal portion.

FIG. 2 shows a catheter 30 having a plurality of segments 12, 14, 16 and a distal portion 40 having a desired curve shape 38. Although the distal portion 40 may be relatively flexible, the catheter 30 may be biased to retain the curve shape 38. The curve shape 38 of the catheter 30 facilitates navigation and positioning of the catheter 30 within tortuous vasculature. The segments 12, 14, 16 each may be comprised of substantially the same material, or they may be comprised of different materials having distinct properties. The catheter 30 may be formed using a plurality of layers such as the catheter 10 of FIG. 1. In one embodiment, only the outer layer 26 has a plurality of segments 12, 14, 16.

Figure 3:
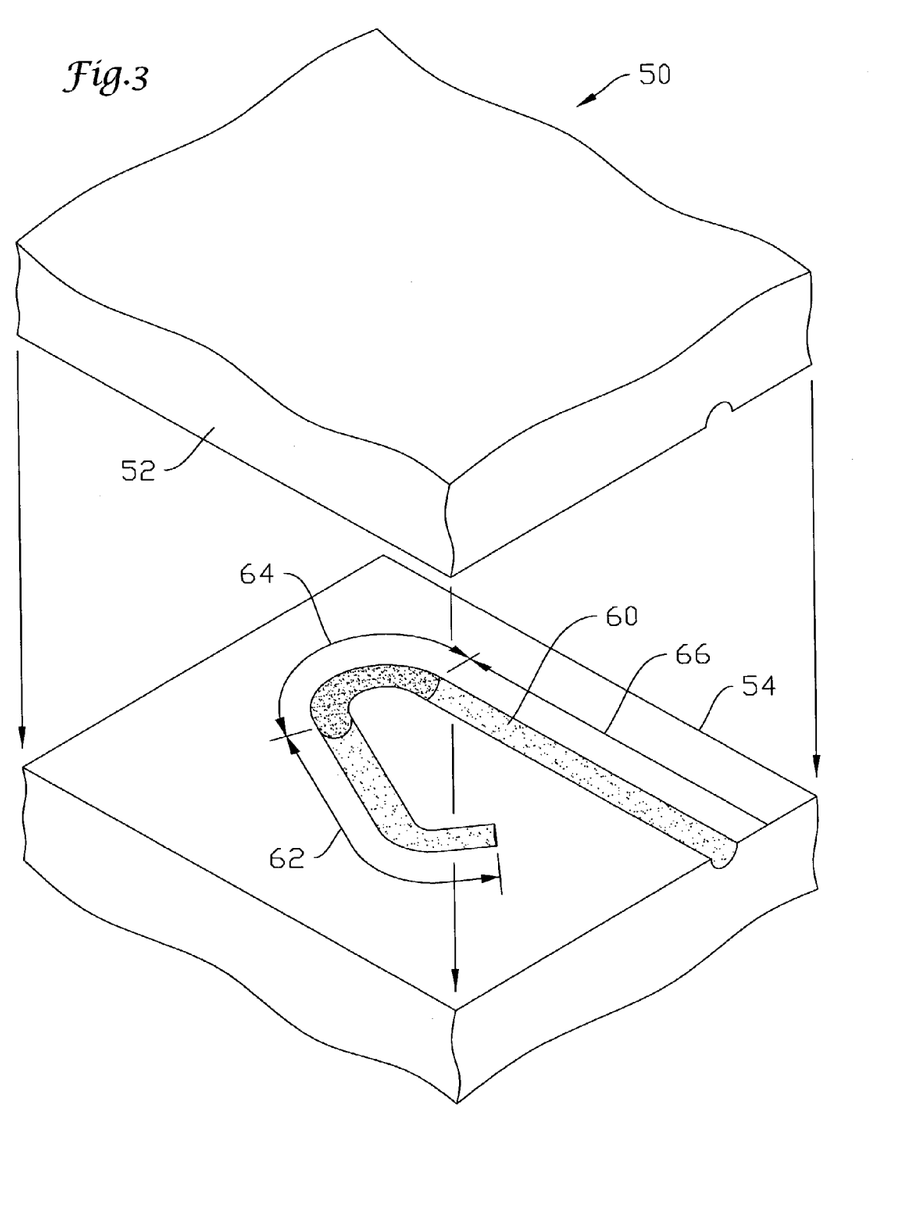
FIG. 3 is a perspective view of a fixture for receiving a catheter tube with the fixture chamber walls having a ferromagnetic material including varied segment concentrations depicted on the surface.
Figure 4:
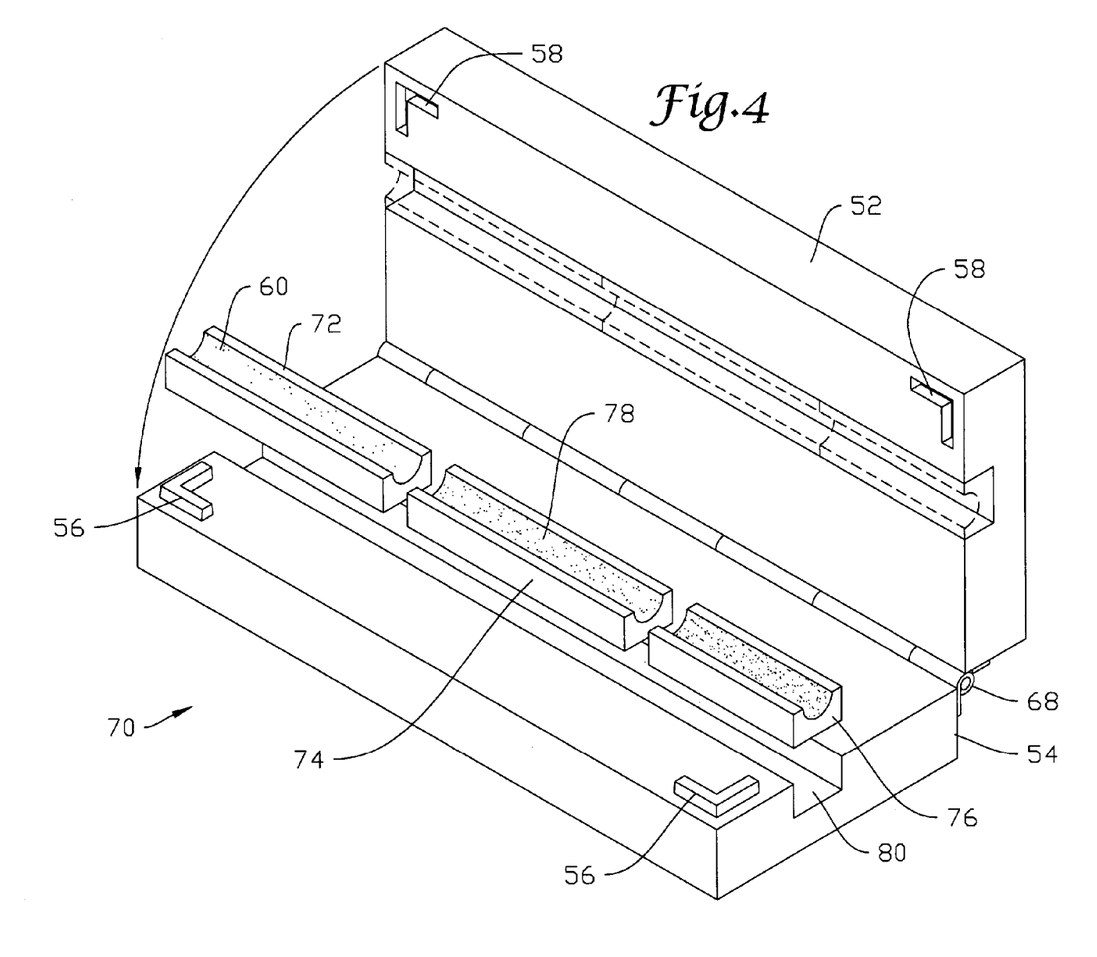
FIG. 4 is a perspective view of a fixture including removable inserts, with the inserts having chamber walls having a ferromagnetic material of varied concentration.

FIGS. 3 and 4 depict two variations of a fixture which can be utilized with the present invention. Elements of one embodiment may be incorporated into another embodiment as necessary. FIG. 3 shows a fixture 50 for forming a catheter such as the catheter 10 depicted in FIG. 1 or a catheter curve such as the catheter curve 38 of the catheter 30 depicted in FIG. 2. The fixture 50 may include a top section 52 and a bottom section 54, or it may only include one section. One skilled in the art will understand that the scope of the invention shall not be limited by the number of sections comprising the fixture. The sections may have a means for securing the sections to one another such as a hinge 68 shown in FIG. 4. The sections 52, 54 may also or alternatively have a means for aligning the sections 52, 54. As in FIG. 4, the bottom section 54 may include tabs 56 and the top section 52 may include slots 58 for receiving the tabs 56.

The fixture 50 has a chamber 60 for receiving at least a portion of the catheter 10, 30. The chamber 60 may have a desired curve shape resembling the desired curve shape 38 of the catheter 30 as FIG. 2 illustrates, or the chamber 60 may be substantially straight as shown in FIG. 4. In one embodiment, the chamber 60 has a plurality of portions 62, 64, 66 having a ferromagnetic material; a first portion 62 having a first selected composition including a ferromagnetic material, a second portion 64 having a second selected composition including a ferromagnetic material, and a third portion 66 having a third selected composition including a ferromagnetic material. Although the chamber 60 shown in FIG. 3 includes three portions 62, 64, 66, the invention is not intended to be limited by the number of portions in the chamber 60.

The selected composition for each portion 62, 64, 66 may be chosen for its unique properties including the Curie temperature of the ferromagnetic material containing portion. A desired Curie temperature may be chosen to correspond to the melting point of the material of the catheter segment 12, 14, 16 in contact with a selected portion 62, 64, 66 of the chamber 60. By having multiple portions 62, 64, 66 with distinct compositions, it is possible to heat different segments 12, 14, 16 of the catheter 10, 30 to different temperatures corresponding to different melting temperatures. Further, selected segments could include insulating material to protect adjacent areas from overheating.

FIG. 4 shows an alternative fixture 70 having a plurality of inserts 72, 74, 76. The inserts 72, 74, 76 are disposed in a channel 80 in the fixture 70. Although FIG. 4 shows a substantially straight channel 80 having inserts 72, 74, 76, the channel 80 may have a curve shape 58 such as the fixture 50 of FIG. 3 for receiving curved inserts. The inserts 72, 74, 76 have a chamber 60 for receiving at least a portion of a catheter 10, 30. In one embodiment, the inserts 72, 74, 76 include a ferromagnetic material. In another embodiment, the inserts have a coating 78 including a ferromagnetic material. As in the chamber 60 of FIG. 3, each insert 72, 74, 76 may include the same ferromagnetic material or it may include a distinct ferromagnetic material. The fixture 70 may have a top section 52 and a bottom section 54 as shown in FIG. 4, or it may only have one section. The top section 52 can include identical inserts to corresponding areas of the bottom section 54. One skilled in the art will understand that the scope of the invention shall not be limited by the number of sections comprising the fixture. A hinge 68 allows the top section 52 to be lifted off the bottom section 54, yet remain coupled together. Additionally or alternatively, tabs 56 of the bottom section 54 may be disposed in slots 58 of the top section 52 in order to securely align the sections 52, 54.

Similarly to the fixture 50 of FIG. 3, the selected composition of a ferromagnetic material for each insert 72, 74, 76 may be chosen for its unique properties such as the Curie temperature of the ferromagnetic material. Further, certain inserts can be made of insulating material to protect adjacent segments from overheating. As explained above, different segments 12, 14, 16 of a catheter 10, 30 may be heated to different temperatures in relation to the Curie temperature of each insert 72, 74, 76.

Figure 5:
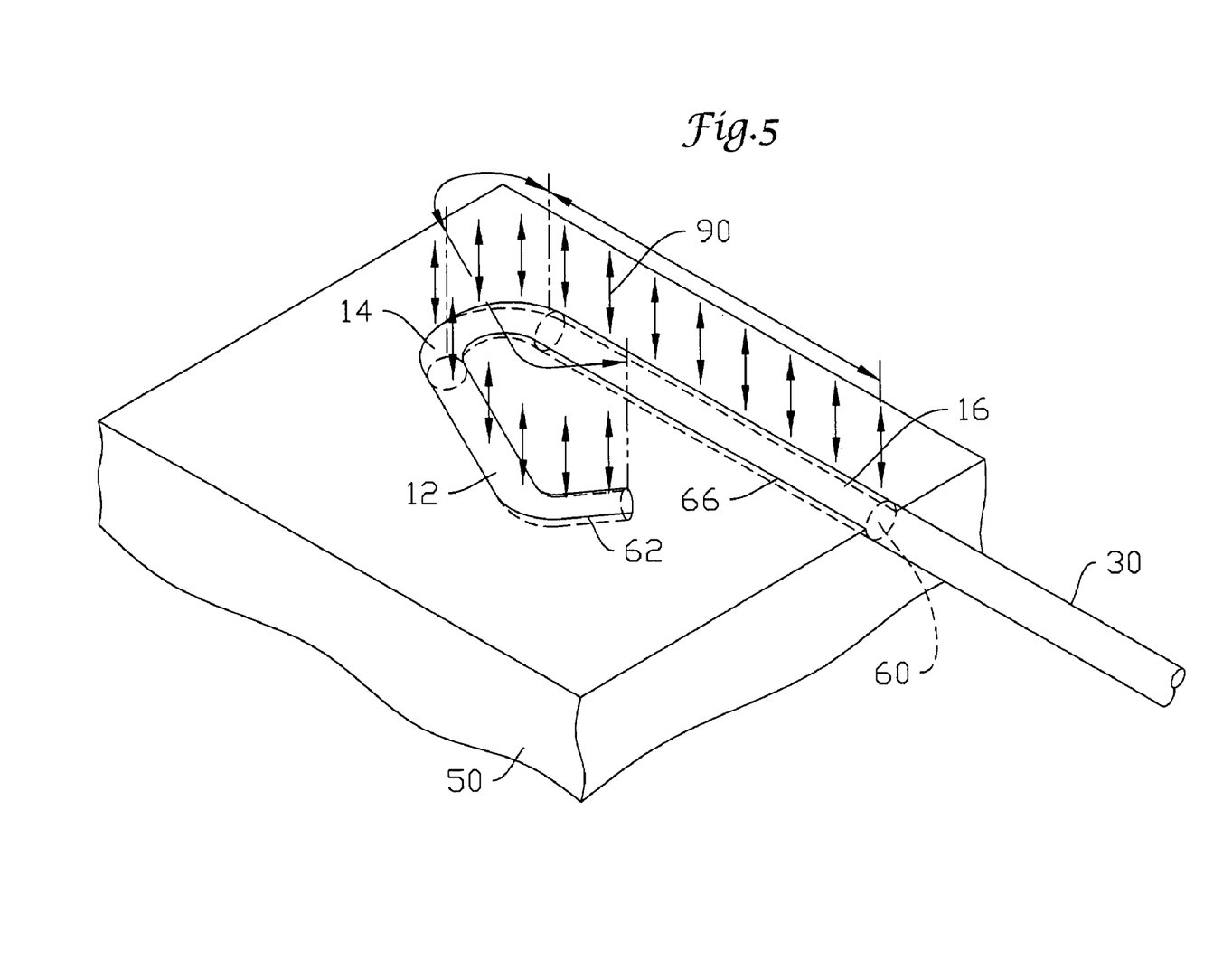
FIG. 5 is a perspective view of a catheter tube positioned in a fixture.

FIG. 5 demonstrates one example of the catheter forming process. A fixture 50 having a chamber 60 for receiving at least a portion of a catheter 30 is provided. The chamber 60 has a plurality of portions 62, 64, 66, each having a composition including a ferromagnetic material. The catheter 30 such as the catheter of FIG. 2 includes a plurality of segments 12, 14, 16 comprising the outer layer 26. A portion of the catheter 30 is placed in the chamber 60, wherein the catheter segments 12, 14, 16 may correspond to the portions 62, 64, 66 of the chamber 60 having a ferromagnetic composition. The fixture 50 and at least a portion of the catheter 30 are exposed to an alternating magnetic field 90. In one embodiment, the alternating magnetic field 90 may be made by using an alternating electrical current. Heat is generated in the fixture 50 due to the hysteresis loss in the ferromagnetic material exposed to the alternating magnetic field 90. The ferromagnetic material may be heated to its corresponding Curie temperature above which point the material no longer heats. A desired Curie temperature may be reached by selectively choosing the particle size and volume fraction of the ferromagnetic material, as well as controlling the effect of oxidation during heat generation. Electromagnetic induction heating in this fashion allows for quick, uniform, controlled, and selective heating of a desired material.

The selected Curie temperature of the ferromagnetic material may be chosen to correspond to the fusing or melting temperature of the segments 12, 14, 16 of the catheter 30. It is, therefore, possible to allow each segment 12, 14, 16 of the catheter 30 to reach its unique fusing or melting point without overheating another portion of the catheter 30. In this fashion, the segments 12, 14, 16 of the catheter 30 may be bonded to the catheter 30 and/or to each other. Additionally or alternatively, a curve shape 38 may be formed in a portion of the catheter 30 through the heating process.

Once the fixture 50 and the selected portion of the catheter 30 reach their desired temperatures, the fixture 50 and the catheter 30 may be removed from the alternating magnetic field 90 and allowed to cool. Another catheter may be placed in the fixture 50 and this process repeated.

Figure 6:
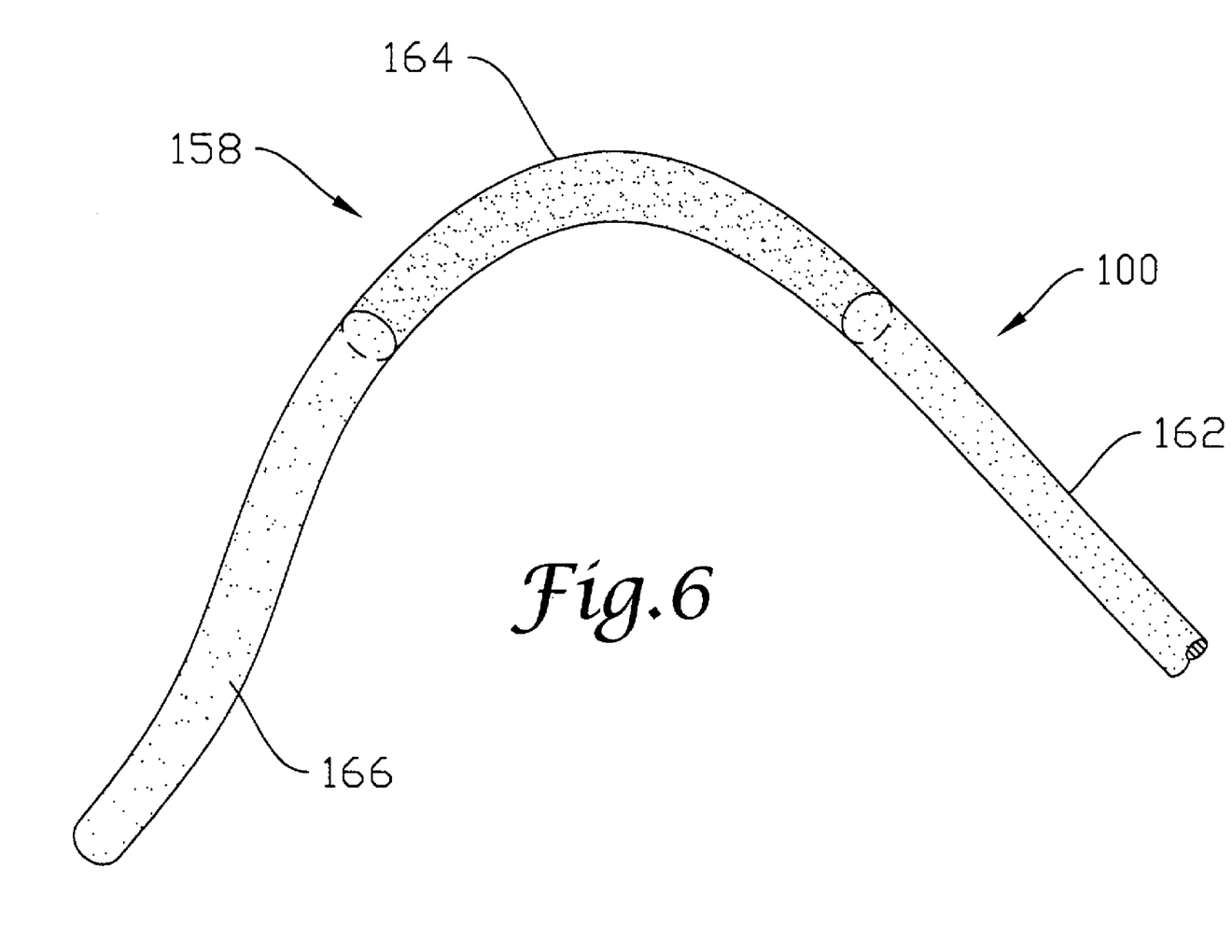
FIG. 6 is a side view of a mandrel having a plurality of ferromagnetic portions.

FIG. 6 shows a mandrel 100 having a plurality of portions 162, 164, 166. The mandrel 100 has a first portion 162 having a first composition including a ferromagnetic material, a second portion 164 having a second composition including a ferromagnetic material, and a third portion 166 having a third composition including a ferromagnetic material. Although the mandrel 100 in FIG. 6 includes three portions 162, 164, 166, the scope of the invention is not limited by the number of portions of the mandrel 100. The portions 162, 164, 166 may include distinct compositions including a ferromagnetic material or they may be substantially the same. The mandrel 100 in FIG. 6 includes a curved distal region 158, but the mandrel 100 may also be substantially straight.

There are a number of possible ways that the mandrel 100 may include a ferromagnetic material. The mandrel 100 may include ferromagnetic particles embedded in the outer surface, or a coating having a composition of a ferromagnetic material. Alternatively, the mandrel may be formed with a mixture of a polymer and ferromagnetic materials or have a core having a ferromagnetic material. The mandrel may be substantially rigid or may be flexibly manipulated.

Figure 7:
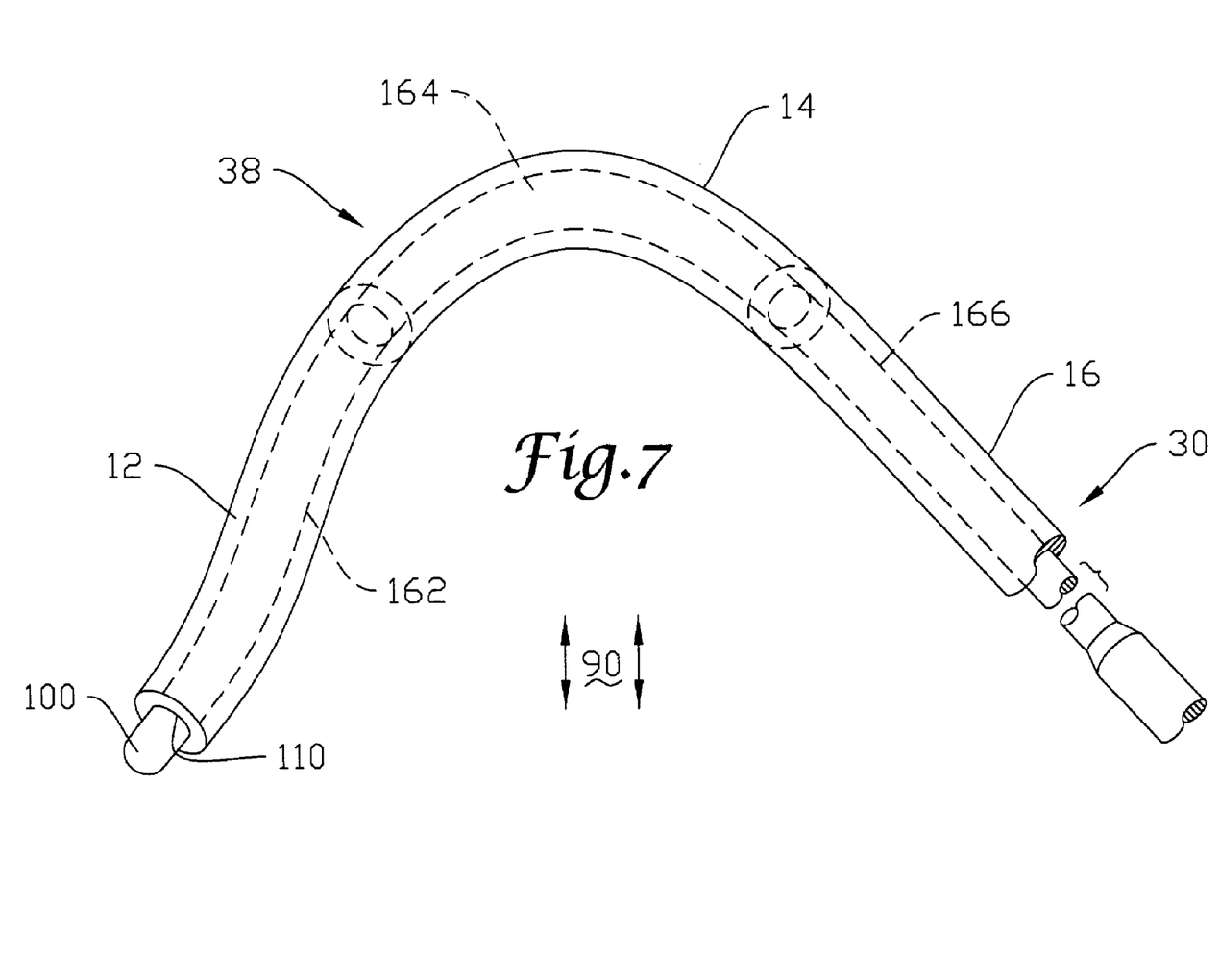
FIG. 7 is a perspective view of a catheter tube having a mandrel disposed within the lumen.

FIG. 7 demonstrates another example of a catheter forming process similar to that of FIG. 5. The mandrel 100 of FIG. 6 is disposed within the lumen 110 of a catheter 30 such as in FIG. 2. In one embodiment, the plurality of portions 162, 164, 166 of the mandrel 100 corresponds to the plurality of segments 12, 14, 16 of the catheter 30. A curve shape 38 may be formed in at least a portion of the catheter 30 disposed around the mandrel 100, or the catheter 30 may be retained substantially straight. The mandrel 100 and at least a portion of the catheter 30 are exposed to an alternating magnetic field 90. The mandrel 100 and the portion of the catheter 30 are allowed to reach a desired temperature preferably selected by designing the portions 162, 164, 166 of the mandrel 100 to have predetermined Curie temperatures. Desired Curie temperatures may be controlled by selectively including a ferromagnetic material in the mandrel 100 as explained above. In this way, the segments 12, 14, 16 of the catheter 30 may reach different temperatures such as their corresponding melting or fusing temperatures without overheating another segment of the catheter 30. As the segments 12, 14, 16 of the catheter 30 reach their respective melting or fusing temperatures, they may be bonded to the catheter 30 and/or to another segment. Additionally or alternatively, a curve shape 38 may be formed in a portion of the catheter 30 through the heating process. Once the catheter 30 is heated to its desired temperature, the mandrel 100 and the catheter 30 may be removed from the alternating magnetic field 90 and allowed to cool. The cooling rate may be controlled to give an annealing effect to the polymers if desired. The mandrel 100 may be removed from the catheter 30 and the forming process repeated.

Figure 8:
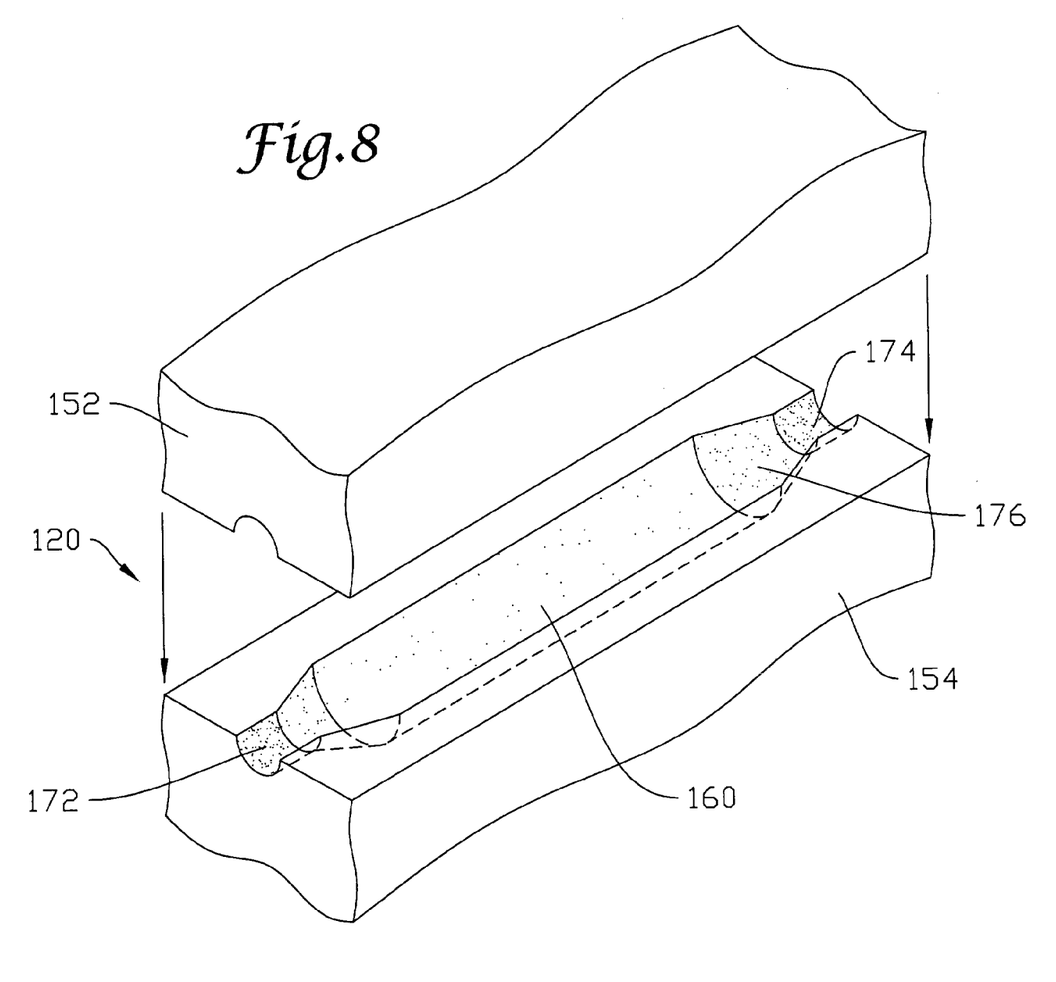
FIG. 8 is a perspective view of a fixture for forming an angioplasty balloon.

Other forming processes similar to those discussed above may prompt a similar use of a ferromagnetic material exposed to an alternating magnetic field 90. FIG. 8 shows a fixture 120 for forming an angioplasty balloon to a catheter using a similar forming process. The fixture 120 may have a top section 152 and a bottom section 154 and may have similar securing features such as the fixtures 50, 70 of FIGS. 3 and 4. The fixture 120 has a chamber 160 for receiving a tubular member which is blow-molded to form a balloon (not shown). Such processes of balloon formation are disclosed in commonly assigned U.S. Pat. No. 5,087,394, the disclosure of which is incorporated herein by reference. The chamber 160 includes a center portion 176 and two end portions 172, 174. The end portions 172, 174 may have a different ferromagnetic material or material concentration/particle size than the center portion 176. Therefore, the end portions 172, 174 may be able to reach a different temperature than the center portion 176 when the fixture 120 is exposed to an alternating magnetic field 90. In this instance, the end portions 172, 174 may reach a higher temperature, which may be desirable due to greater end portion thicknesses while retaining the center portion of the balloon at or below a desired maximum temperature of the center balloon material. Therefore, the balloon could be heat treated preferentially in the fixture during heating and cooling cycles.

It should be understood that this disclosure is, in many respects only illustrative. Changes may be made in details, particularly in matters of shape, size, arrangement of parts, and order of steps without departing from the scope of the invention. The language of the appended claims shall define the scope of the invention.

What is claimed is:

1. A method for forming a curve in a catheter tube comprising the steps of:
    providing a catheter tube having a lumen therethrough;
    providing a means for electromagnetic induction heating of the catheter tube, the means having a composition including a selected amount of a ferromagnetic material having a Curie temperature;
    placing at least a portion of the catheter tube in close proximity to the means for electromagnetic induction heating of the catheter tube;
    shaping the at least a portion of the catheter tube in a desired curve shape;
    exposing the at least a portion of the catheter tube and the means for electromagnetic induction heating of the catheter tube to an alternating magnetic field such that the means for electromagnetic induction heating of the catheter tube reaches the Curie temperature;
    wherein the step of shaping the at least a portion of the catheter tube in a desired curve shape is performed prior to exposing the at least a portion of the catheter tube and the means for electromagnetic induction heating of the catheter tube to an alternating magnetic field; and
    separating the catheter tube from the means for electromagnetic induction heating of the catheter tube;
    wherein the means for electromagnetic induction heating of the catheter tube includes a plurality of portions including at least a first portion having a first selected amount of a ferromagnetic material having a first Curie temperature and a second portion having a second selected amount of a ferromagnetic material having a second Curie temperature different from the first Curie temperature.

2. The method of claim 1, wherein the second portion of the means for electromagnetic induction heating reaches the second Curie temperature.

3. The method of claim 1, wherein the catheter tube has at least two portions, wherein at least one portion of the means for electromagnetic induction heating corresponds with at least one portion of the catheter tube.

4. A method for forming a curve in a catheter tube comprising the steps of:
    providing a catheter tube having a lumen therethrough;
    providing a mandrel having a composition including a selected amount of a ferromagnetic material having a Curie temperature;
    disposing the mandrel within at least a portion of the lumen of the catheter tube;
    shaping the at least a portion of the catheter tube in a desired curve shape;
    exposing the at least a portion of the catheter tube and the mandrel to an alternating magnetic field such that the mandrel is heated to the Curie temperature;
    wherein the step of shaping the at least a portion of the catheter tube in a desired curve shape is performed prior to exposing the at least a portion of the catheter tube and the mandrel to an alternating magnetic field; and
    removing the mandrel from the catheter tube;
    wherein the mandrel includes at least a first portion having a first selected amount of a ferromagnetic material having a first Curie temperature and a second portion having a second selected amount of a ferromagnetic material having a second Curie temperature different from the first Curie temperature, wherein the second portion of the mandrel is heated to the second Curie temperature.

5. A method for forming a curve in a catheter tube comprising the steps of:
    providing a catheter tube having a lumen therethrough;
    providing a fixture having a chamber with a desired curve shape for receiving at least a portion of the catheter tube, the fixture having a composition including a selected amount of a ferromagnetic material having a Curie temperature;
    inserting at least a portion of the catheter tube into the fixture;
    shaping the at least a portion of the catheter tube into the desired curve shape of the chamber;
    exposing the fixture and the at least a portion of the catheter tube to an alternating magnetic field such that the fixture is heated to the Curie temperature;
    wherein the step of shaping the at least a portion of the catheter tube in a desired curve shape of the chamber is performed prior to exposing the fixture and the at least a portion of the catheter tube to an alternating magnetic field; and
    removing the catheter tube from the fixture;
    wherein the fixture includes at least a first portion having a first selected amount of a ferromagnetic material having a first Curie temperature and a second portion having a second selected amount of a ferromagnetic material having a second Curie temperature different from the first Curie temperature, wherein the second portion of the fixture reaches the second Curie temperature.

6. A method of forming a curve in a catheter tube comprising the steps of:
    providing a catheter tube having a lumen therethrough;
    providing a means for electromagnetic induction heating of the catheter tube, the means having a first composition including a selected amount of a ferromagnetic material having a first Curie temperature and the means having a second composition including a selected amount of a ferromagnetic material having a second Curie temperature different from the first Curie temperature;

placing at least a portion of the catheter tube in close proximity to the means for electromagnetic induction heating of the catheter tube;

shaping the at least a portion of the catheter tube in a desired curve shape;

exposing the at least a portion of the catheter tube and the means for electromagnetic induction heating of the catheter tube to an alternating magnetic field such that the means for electromagnetic induction heating of the catheter tube reaches the first Curie temperature; and separating the catheter tube from the means for electromagnetic induction heating of the catheter tube.

7. The method of claim 6, wherein the means for electromagnetic induction heating of the catheter tube retains at least a portion of the catheter tube in the desired curve shape.

8. The method of claim 7, wherein the means for electromagnetic induction heating of the catheter tube includes a mandrel disposed within the lumen of the catheter tube.

9. The method of claim 7, wherein the means for electromagnetic induction heating of the catheter tube includes a fixture having a chamber for receiving at least a portion of the catheter tube.

10. The method of claim 6, wherein a first portion of the means for electromagnetic induction heating of the catheter tube reaches the first Curie temperature and a second portion of the means for electromagnetic induction heating of the catheter tube reaches the second Curie temperature.

* * * * *